United States Patent [19]

Buckles

[11] 4,326,510

[45] Apr. 27, 1982

[54] BARRIER CONTRACEPTIVE TORUS

[75] Inventor: Richard G. Buckles, Basel, Switzerland

[73] Assignee: World Health Organization, Geneva, Switzerland

[21] Appl. No.: 96,156

[22] Filed: Nov. 20, 1979

[51] Int. Cl.³ .............................................. A61F 5/46
[52] U.S. Cl. .................................... 128/127; 128/260
[58] Field of Search .............................. 128/127–130, 128/260–261; 424/15

[56] References Cited

U.S. PATENT DOCUMENTS

| | | | |
|---|---|---|---|
| 3,545,439 | 12/1970 | Duncan | 128/260 |
| 3,699,951 | 10/1972 | Zaffaroni | 128/130 |
| 3,777,015 | 12/1973 | Zaffaroni | 424/15 |
| 3,845,761 | 11/1974 | Zaffaroni | 128/130 |
| 3,854,480 | 12/1974 | Zaffaroni | 128/260 |
| 3,948,254 | 4/1976 | Zaffaroni | 128/127 |
| 3,952,737 | 4/1976 | Lipfert et al. | 128/127 |
| 3,995,633 | 12/1976 | Gougeon | 128/127 |
| 4,007,249 | 2/1977 | Erb | 128/127 |
| 4,066,075 | 1/1978 | Hughes | 128/127 |
| 4,198,965 | 4/1980 | Strickman et al. | 128/127 |
| 4,200,090 | 4/1980 | Drobish | 128/127 |
| 4,219,016 | 8/1980 | Drobish et al. | 128/130 |

FOREIGN PATENT DOCUMENTS 2158226  5/1973  Fed. Rep. of Germany .

OTHER PUBLICATIONS

Parfar International Workshop on New Developments in Vaginal Contraception, World Health Organization.

Primary Examiner—C. Fred Rosenbaum
Attorney, Agent, or Firm—Cushman, Darby & Cushman

[57] ABSTRACT

A barrier contraceptive device and a method for preventing conception utilizing the device. The device comprises a torus of biocompatible material sized to fit in a vagina, structure—such as overlapping flaps—being provided with the torus for providing a primary barrier preventing direct ejaculation into the cervix while allowing fluid drainage from the cervix. The material forming the torus contains a spermicide and is operative to allow release of the spermicide to maintain an effective level of spermicide in the area between the torus and the cervix to kill any sperm that passes the primary barrier. The torus is constructed so that the spermicide is more readily releasable through the inner peripheral surface thereof than the outer peripheral surface thereof. The torus releases an effective amount of spermicide approximately over a period of time from the last day of menses until the start of the next menstrual period, the torus being inserted about the last day of menses and removed and disposed of at about the start of the next menstrual period.

10 Claims, 10 Drawing Figures

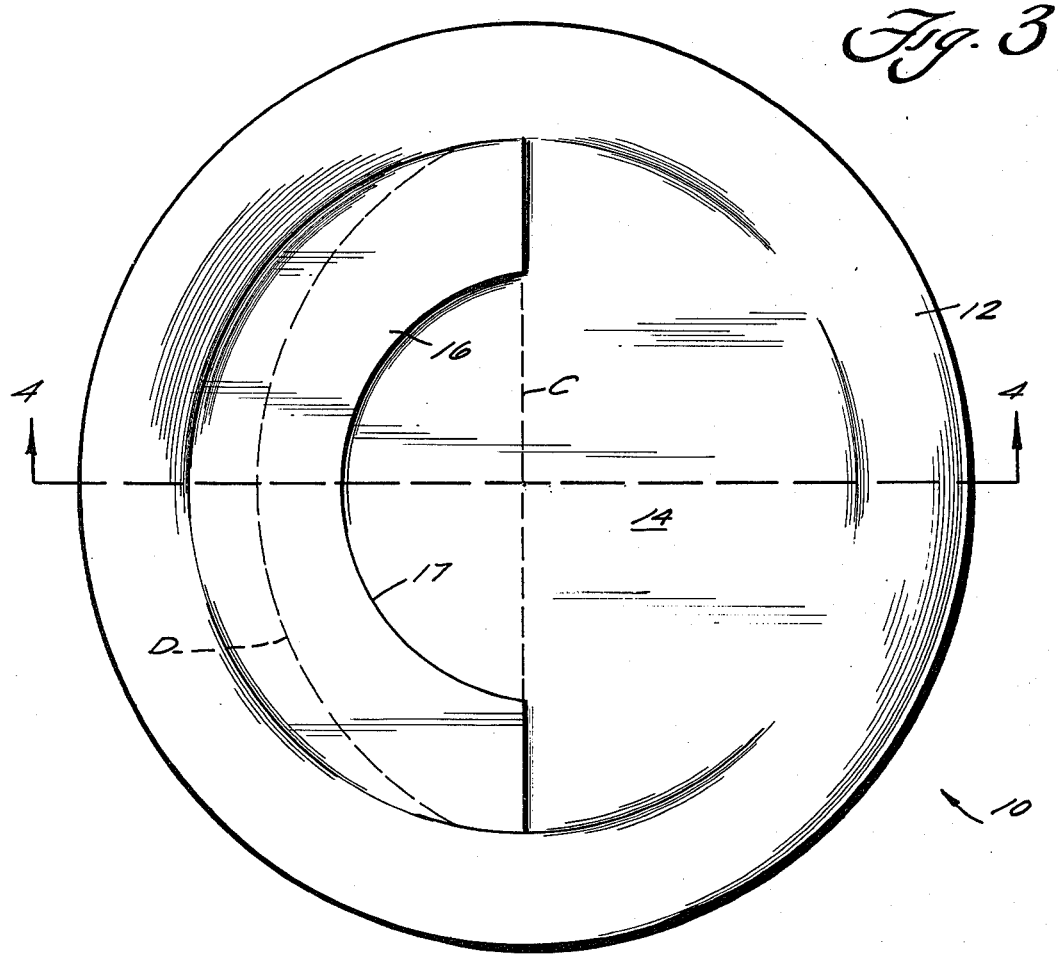
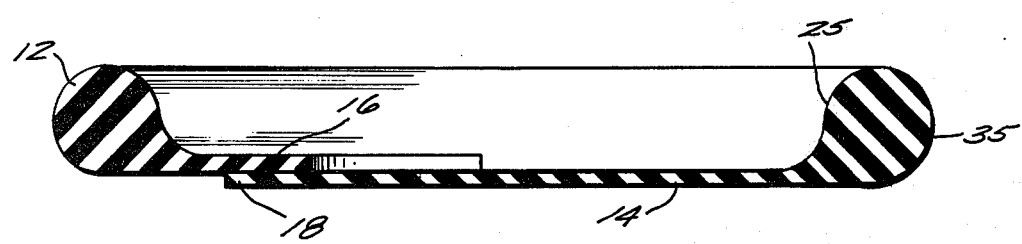
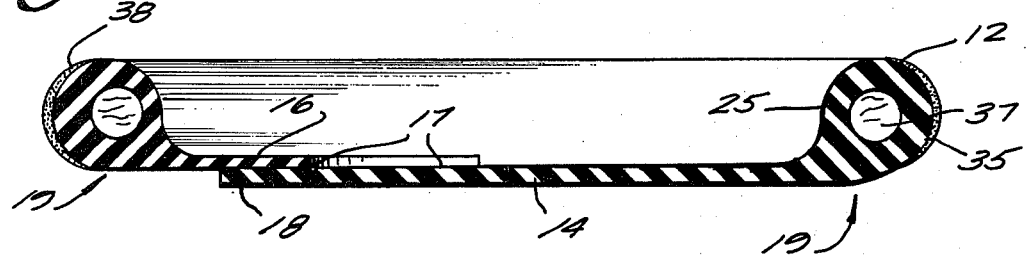

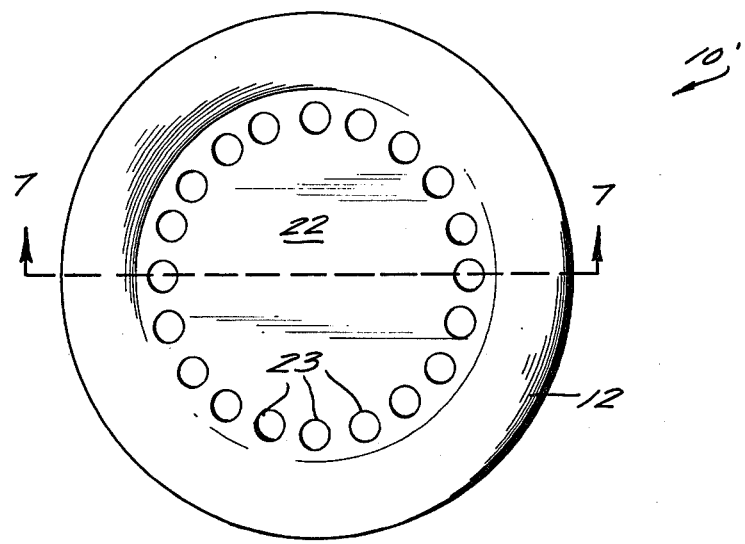
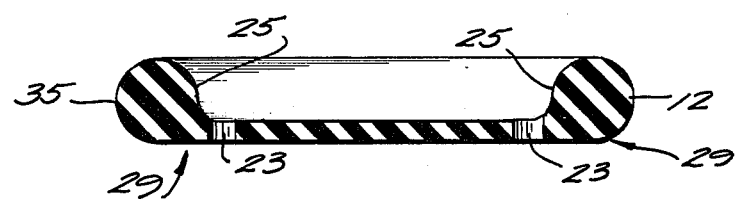
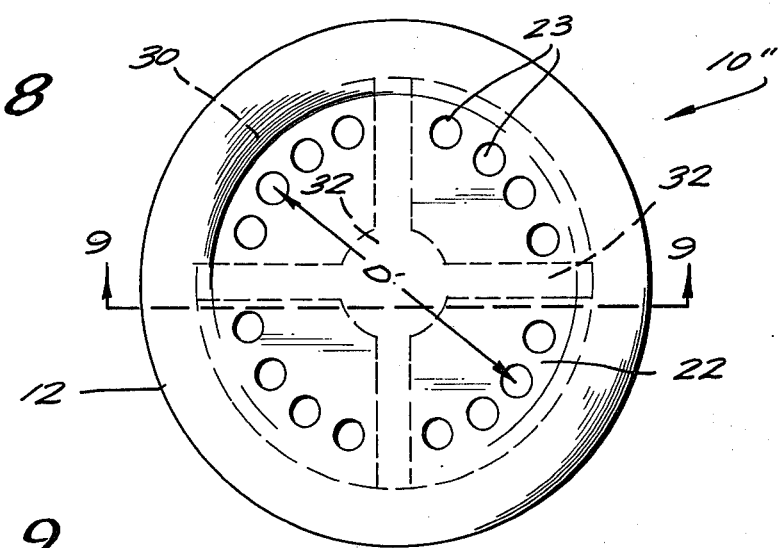
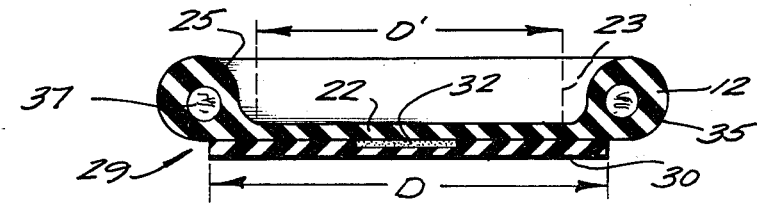

BARRIER CONTRACEPTIVE TORUS

BACKGROUND AND SUMMARY OF THE INVENTION

There have been developed a wide variety of spermicide releasing devices for placement in the vagina for providing an effective level of spermicide within the vagina, such as described in an article by F. G. Burton, et al in CONTRACEPTION 17, pages 221-230, 1978, entitled "Fabrication and Testing of Vaginal Contraceptive Devices Designed for Release of Pre-Specified Dose Levels of Steroids", and U.S. Pat. No. 3,545,439 (the disclosure of which is hereby incorporated by reference herein). There also have been a wide variety of devices used for barrier methods of contraception, such as conventional diaphragms. While most of such devices are generally effective, there are a number of drawbacks associated with each.

Conventional barrier diaphragms have not been satisfactory for large fractions of the population because of the need to insert the barrier diaphragm, coated with a spermicidal formulation, within a few hours of coitus, the need to add additional spermicide if coitus is repeated, the need to remove the diaphragm after usage due to build up of unacceptable odors and/or the discomfort of the occlusive fit within the vagina, and the general unacceptability surrounding the "messiness" of the insertion, removal, and washing procedure for reuse. While vaginal rings releasing spermicide overcome some of the above-mentioned drawbacks associated with barrier diaphragms, in most instances they have not been demonstrated to be entirely effective in preventing conception.

According to the present invention, a contraceptive device is provided which overcomes most of the drawbacks associated with conventional barrier diaphragms and vaginal rings. The device according to the invention comprises a torus of biocompatible material sized to fit in a vagina, and has means formed therewith for providing a primary barrier preventing direct ejaculation into the cervix while allowing fluid drainage from the cervix. The device is designed to be disposable after one use (one menstrual period), is readily insertable, and can be constructed to allow release (e.g., diffusion) of spermicide therefrom at an effective level in the area between the device and the cervix to kill any sperm that pass the primary barrier. The device may be constructed so that the spermicide is more readily releasable through the inner peripheral surface thereof than through the outer peripheral surface thereof.

The device according to the present invention may be worn from the last of menses until the start of the next menstrual period. There is no "messiness" associated therewith since the spermicide is contained internally. The device may be discarded after one use, being relatively inexpensive to fabricate. While providing an effective barrier preventing direct ejaculation into the cervix, it alows fluid drainage in the opposite direction so that odors are minimized. The spermicide can be released in combination with a surfactant and/or foaming agent, and it permits complete mixing and spreading in the adjacent area so as to maintain a desired spermicidal concentration.

It is the primary object of the present invention to provide an effective, readily utilizable contraceptive device, and method of preventing conception utilizing same. This and other objects of the invention will become clear from an inspection of the detailed description of the invention and from the appended claims.

BRIEF DESCRIPTION OF THE DRAWINGS

FIG. 3 is a rear plan view of the device of FIGS. 1 and 2;

FIGS. 4a and 4b are sectional views taken along lines 4—4 of FIG. 3 of different internal configuration embodiments of the device of FIG. 3;

FIG. 6 is a rear plan view of a second exemplary embodiment of a device according to the invention;

FIG. 7 is a sectional view taken along lines 7—7 of FIG. 6;

FIG. 8 is a front plan view of a third exemplary embodiment of a device according to the invention; and FIG. 9 is a sectional view taken along lines 9—9 of FIG. 8.

DETAILED DESCRIPTION OF THE INVENTION

Figure 1:
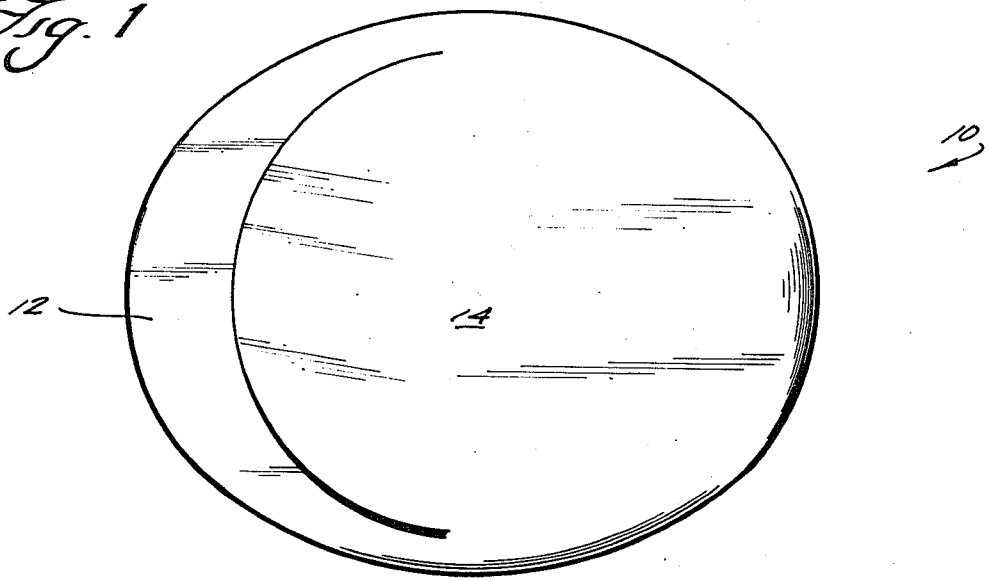
FIG. 1 is a front perspective view of one exemplary embodiment of the device according to the present invention.
Figure 2:
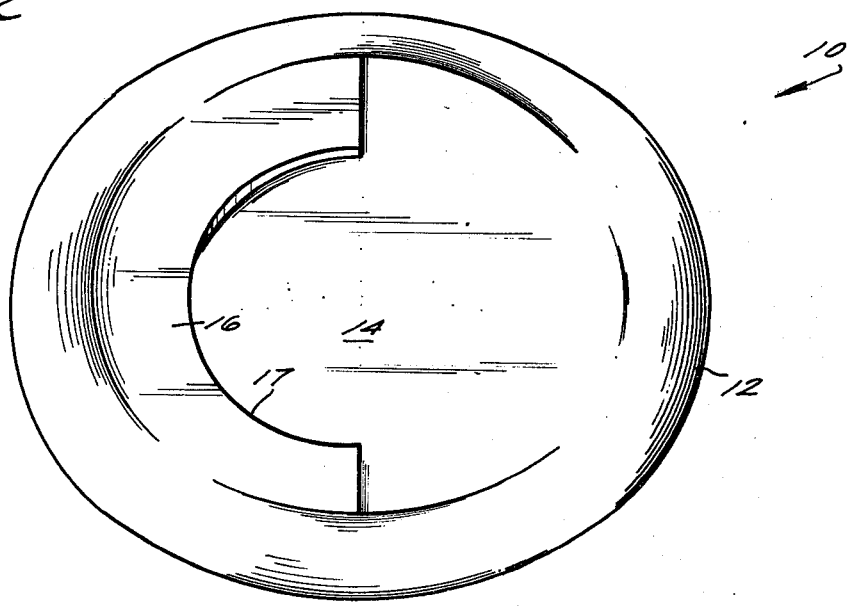
FIG. 2 is a rear perspective view of the device of FIG. 1.

The three different embodiments of an exemplary contraceptive device according to the present invention are illustrated generally at 10, 10', and 10'' in FIGS. 1, 6 and 8, respectively. In each embodiment the device comprises a torus 12 of biocompatible material sized to fit in a vagina V (see FIG. 5). The torus has means associated therewith for providing a primary barrier preventing direct ejaculation into the cervix C of the uterus U (see FIG. 5) while allowing fluid drainage from the cervix C. In each of the embodiments 10, 10', 10'', such barrier-providing means takes a different form.

In the embodiment of FIGS. 1-4, the means for providing a primary barrier while allowing fluid drainage takes the form of a pair of overlapping flaps 14, 16 extending into and completely covering the interior opening of the torus 12. The flap 16 is arcuate in shape and extends approximately 180° around the opening in the torus, defining a circular segment central opening bounded by the interior edge of the flap 16 and the dotted line C in FIG. 3. The flap 14 is of flexible material and is generally circular in shape, and extends approximately 360° around the opening in the torus, having an overlapping portion 18 (the area between the dotted line D and the interior edge 17 of the flap 16 in FIG. 3) extending over the flap 16. The overlapping portion is defined generally by the dotted lines D, C of the flap 14 in FIG. 3. As illustrated in the drawings, it is preferred that the flaps 14, 16 be provided on one end of the torus 12 (providing an end closed face for the torus), and the flaps 14, 16 make smooth junctions with the torus, as can be seen in FIG. 1 and as indicated generally at 19 in FIGS. 4a and 4b.

Figure 5:
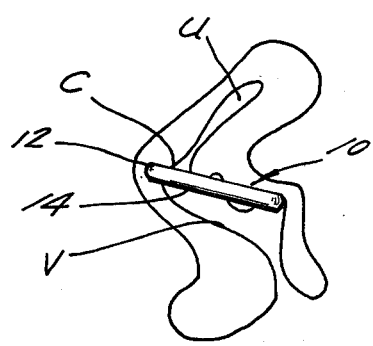
FIG. 5 is a schematic view showing the correct placement of the device in a human vagina.

In utilizing the embodiment device 10 illustrated in the drawings to prevent conception, as indicated in FIG. 5 the torus 12 is placed so that the end thereof containing the flaps 14, 16 is furthest from the uterus U. The flaps 14, 16 thus overlap during the ejaculation, yet fluid can drain from the cervix C and pass through the area defined by the dotted line C and edge 17 of flat 16, underneath the overlapping portion 18 of flap 14, to drain into the vagina V. In a modification of the device 10 with the flap 14 interior (with respect to the torus) of the flap 16, the device would be positioned so that the end containing the flaps 14, 16 was closest to the uterus U.

In both the devices 10', 10", the means for providing a primary barrier while allowing fluid drainage comprises a first circular member 22 of biocompatible material extending from the torus and covering the opening in the torus, and means defining a plurality of openings 23 around the perimeter of the member 22 just inside the interior periphery 25 of the torus 12. The circular member 22 preferably is provided on one end of the torus, as can be seen in FIGS. 7 and 9, and makes smooth junctions indicated generally at 29 in the drawings, with the torus 12.

The device 10" further comprises a second circular member 30 of flexible biocompatible material which overlays the first circular member 22. The distance D is the distance a pair of opposite openings 23 are spaced from each other. Also, means are provided for attaching the second member 30 to the first members so that the members are substantially concentric and perimeter portions of the second member 30 overlie the openings 23 in the first member 22. Such attaching means may comprise a suitable adhesive disposed between portions of the members 22, 30, a suitable pattern such adhesive could take being illustrated in dotted line generally at 32 in FIG. 8.

The torus 12 further includes means associated therewith for maintaining an effective level of spermicide in the area between the device 10, 10', 10" and cervix C to kill any sperm that may pass the primary barrier. Such means may be provided by forming the torus 12 of a material having characteristics such that spermicide may be incorporated therewith and released therefrom. A wide variety of known materials, especially elastomers and thermoplastic materials, have such characteristics. Suitable materials include natural rubber, cis-polyisoprene, polydimethyl siloxane, butyl rubber, ethylenevinyl acetate, polyethylene, and the like. A wide variety of such suitable materials are disclosed in U.S. Pat. Nos. 3,545,439 and 3,845,761, the disclosures of which are hereby incorporated by reference herein. The spermicide may be incorporated in the material in a wide variety of manners also, such as incorporating the spermicide directly with the material during formation thereof, disposition of the spermicide in crystalline form (such as in U.S. Pat. No. 3,854,480) or forming the torus so that it is hollow, the interior peripheral surface 25 and the outer peripheral surface 35 of the torus 12 defining a reservoir therebetween, which reservoir can be filled with spermicide in fluid form (such a reservoir arrangement is disclosed in U.S. Pat. No. 3,845,761). In the embodiment of the device illustrated in FIGS. 4a and 7, no interior reservoir is provided (the spermicide, when utilized, being incorporated directly with the torus material), while in the illustrations in FIGS. 4a and 9 an interior reservoir 37 is provided.

Preferably the spermicide is in fluid dosage form, and additionally may contain a surfactant capable of assisting in wetting surfaces to ensure mixing of the spermicide with cervical mucus, and/or a foaming agent for producing foaming during coitus. Suitable surfactants that may be utilized include Tween 20, Tween 80, and other nonionic agents utilized in conventional contraceptive jellies; suitable foaming agents include Tween polyoxyethoxylated molecules, and materials that give off $CO_2$ when reacting with water. A wide variety of conventional spermicides may be utilized, such as nonoxynol-9.

According to the present invention, it is also desirable to construct the torus 12 so that the spermicide contained therein is more readily released through the inner peripheral surface 25 thereof than the outer peripheral surface 35 thereof, so that the spermicide is primarily released above the primary barrier. This may be accomplished, especially where a reservoir 37 is provided, by forming the inner peripheral surface 25 so that it is thinner than the outer peripheral surface 35, as illustrated in FIGS. 4b and 9. Alternatively, or in addition, the outer peripheral surface 35 may be formed of a material, or coated with a material, that does not allow significant release (e.g., diffusion) of spermicide therethrough. Such a coating is illustrated generally at 38 in FIG. 4b, and suitable coating materials are polyvinylidene chloride, cross-linked polyvinyl alcohol, and crystalline polyethylene.

The devices 10, 10', 10" are utilizable in a method of preventing conception in a female (e.g., human) capable of conception. A preferred method is practiced by forming the torus 12 of material capable of incorporating sufficient spermicide to release an effective amount thereof approximately over a period of time from the last day of menses until the start of the next menstrual period, and incorporating sufficient spermicide in the torus to be continuously released at an effective rate from the last day of menses until the start of the next menstrual period. Then the torus is inserted in the female's vagina V about the last day of menses, and positioned so as to provide a primary barrier preventing direct ejaculation into the cervix while allowing fluid drainage from the cervix. When utilizing the embodiment of the device 10 illustrated in the drawings, it is placed so that the end of the torus 12 defined by the flaps 14, 16 is further from the uterus than the open end of the torus, and in utilizing the device 10' it is inserted so that the circular member 30 is further from the uterus than the circular member 22. The torus continuously releases spermicide above the primary barrier. The method is concluded by removing and disposing of the torus at about the start of the next menstrual period.

Thus, it will be seen that according to the present invention a contraceptive device, and method of utilization thereof in the prevention of conception, has been provided that forms a primary barrier while still allowing drainage of fluid from the cervix, and additionally continuously releases an effective dosage of spermicide therefrom. The device is utilized for the entire time between menstrual periods, does not have objectionable "messiness" during insertion, can be discarded after one use (one menstrual period), and performs its primary contraceptive function effectively.

While the invention has been herein shown and described in what is presently conceived to be the most practical and preferred embodiments thereof, it will be apparent to those of ordinary skill in the art that many modifications may be made thereof within the scope of the invention, which scope is to be accorded the broadest interpretation of the appended claims so as to encompass all equivalent structures and methods.

What is claimed is:

1. A contraceptive device comprising:
    a torus of biocompatible materials sized to fit in a vagina;

means formed with the torus for providing a primary barrier preventing direct ejaculation into the cervix while allowing fluid drainage from the cervix;

said means comprising a pair of overlapping flaps, each extending into, and together completely covering, the interior opening of the torus; and one of said flaps being arcuate in shape and extending approximately 180° around the opening in the torus, defining a circular segment central opening; and the other of said flaps being of flexible material and being generally circular in shape extending approximately 360° around the opening in the torus and overlapping portions of the said one flap over the entire arcuate extent thereof.

2. A device as recited in claim 1 wherein said flaps are provided on one end of said torus and make smooth junctions with said torus.

3. A device as recited in claim 1 further comprising means associated with said torus for maintaining an effective level of spermicide in the adjacent area to kill any sperm that pass the primary barrier, said means comprising the material of which said torus is composed having characteristics such that it may have spermicide incorporated therewith, and wherein spermicide is incorporated therewith.

4. A device as recited in claims 1 or 3 wherein the torus material is selected from the group consisting essentially of silicone rubber, natural rubber, cis-polyisoprene, polydimethyl siloxane, butyl rubber, polyethylene, and ethylenevinyl acetate.

5. A contraceptive device comprising
a torus of biocompatible materials sized to fit in a vagina;
means formed with said torus for providing a primary barrier preventing direct ejaculation into the cervix while allowing fluid drainage from the cervix; and
means associated with said torus for maintaining an effective level of spermicide in the adjacent area to kill any sperm that pass the primary barrier, said means comprising the material of which said torus is composed having characteristics such that it may have spermicide incorporated therewith; and wherein spermicide is incorporated therewith in combination with: a surfactant capable of assisting in wetting surfaces to ensure mixing of spermicide with cervical mucus; and a foaming agent for producing foaming during coitus.

6. A device as recited in claim 5 wherein the spermicide is nonoxynol-9.

7. A contraceptive device comprising
a torus having inner and outer peripheral surfaces and sized to fit in a vagina and made of biocompatible material having characteristics such that spermicide is incorporated therewith and is released therethrough to maintain an effective level of spermicide in the area between the device and a cervix with which it is associated; the spermicide being in combination with: a surfactant capable of assisting in wetting surfaces to ensure mixing of spermicide with cervical mucus; and a foaming agent for producing foaming during coitus; and
said torus being constructed so that spermicide contained therein is more readily released through the inner peripheral surface thereof than the outer peripheral surface thereof.

8. A method of preventing conception in a femal capable of conception, utilizing a torus of biocompatible material having means associated therewith for providing a primary barrier preventing direct ejaculation into the cervix while allowing fluid drainage from the cervix, said method comprising the steps of forming the torus of material capable of incorporating sufficient spermicide to release an effective amount thereof approximately over a period of time from the last day of menses until the start of the next menstrual period, the spermicide including a surfactant effective to assist in wetting surfaces so as to assure mixing of spermicide with cervical mucus, and a foaming agent to product foaming during coitus;

constructing the torus so that substantially all of the spermicide releases through the inner peripheral surface thereof and substantially no spermicide releases through the outer peripheral surface thereof;

incorporating sufficient spermicide in the torus to be continuously released at an effective rate from the last day of menses until the start of the next menstrual period;

inserting the torus in the female's vagina about the last day of menses, and positioning it so as to provide a primary barrier preventing direct ejaculation into the cervix while allowing fluid drainage from the cervix; the torus continuously releasing spermicide; and removing and depositing of the torus at about the start of the next menstrual period.

9. A contraceptive device comprising
a torus body of biocompatible materials sized to fit in a vagina and defining a central opening;
means formed with said torus body for providing a primary barrier preventing direct ejaculation into the cervix while allowing fluid drainage from the cervix, said means comprising a valve disposed in said central opening;
means associated with said torus for maintaining an effective level of spermicide in the adjacent area to kill any sperm that pass the primary barrier, said means comprising the material of which said torus body is composed having spermicide incorporated therewith;
said torus body having inner and outer peripheral surfaces respectively adjacent and spaced from said central opening; and
the torus body having a hollow interior which comprises a reservoir of spermicide, and wherein the torus body inner and outer peripheral surfaces are adjacent the reservoir, and wherein the inner peripheral surface of the torus body is thinner than the outer peripheral surface thereof.

10. A contraceptive device comprising
a torus body of biocompatible materials sized to fit in a vagina and defining a central opening;
means formed with said torus for providing a primary barrier preventing direct ejaculation into the cervix while allowing fluid drainage from the cervix;
means associated with said torus for maintaining an effective level of spermicide in the adjacent area to kill any sperm that pass the primary barrier, said means comprising the material of which said torus body is composed having spermicide incorporated therewith; and
said torus body having inner and outer peripheral surfaces respectively adjacent and spaced from said central opening, with the outer peripheral surface of the torus body being coated with a material, distinct from the torus material, that does not allow significant release of spermicide therethrough, so that spermicide incorporated therewith is more readily releasable through the inner peripheral surface thereof than the outer peripheral surface thereof.

* * * * *